US009162059B1

(12) United States Patent
Lindenthaler

(10) Patent No.: US 9,162,059 B1
(45) Date of Patent: Oct. 20, 2015

(54) METHOD FOR FACIAL NERVE STIMULATION OF AGING OR DYSFUNCTIONAL MUSCLES

(71) Applicant: MED-EL Elektromedizinische Geraete GmbH, Innsbruck (AT)

(72) Inventor: Werner Lindenthaler, Oberperfuss (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 0 days.

(21) Appl. No.: 14/316,923

(22) Filed: Jun. 27, 2014

Related U.S. Application Data

(63) Continuation-in-part of application No. 12/582,990, filed on Oct. 21, 2009, now Pat. No. 8,792,989.

(60) Provisional application No. 61/107,081, filed on Oct. 21, 2008, provisional application No. 61/840,014, filed on Jun. 27, 2013.

(51) Int. Cl.
*A61N 1/00* (2006.01)
*A61N 1/36* (2006.01)

(52) U.S. Cl.
CPC ................. *A61N 1/36003* (2013.01)

(58) Field of Classification Search
CPC ... A61N 1/0526; A61N 1/328; A61N 1/0551; A61N 1/36003; A61N 1/36185; A61B 5/04085; A61H 2205/022
See application file for complete search history.

(56) References Cited

U.S. PATENT DOCUMENTS

| 3,279,468 A | 10/1966 | Le Vine ........................ 128/410 |
| 3,851,651 A * | 12/1974 | Icenbice, Jr. .................... 607/66 |
| 4,165,750 A | 8/1979 | Aleev et al. ................... 128/422 |

(Continued)

FOREIGN PATENT DOCUMENTS

| FR | 2279376 | 2/1976 | ............... A61H 1/00 |
| WO | WO 03/020363 | 3/2003 | ............... A61N 1/00 |

(Continued)

OTHER PUBLICATIONS

Angelov et al., "Axonal Branching and Recovery of Coordinated Muscle Activity after Transection of the Facial Nerve in Adult Rats," Adv. Anat. Embryol. Cell Bio., vol. 180, pp. 1-130, 2005.

(Continued)

*Primary Examiner* — Robert N Wieland
(74) *Attorney, Agent, or Firm* — Sunstein Kann Murphy & Timbers LLP

(57) ABSTRACT

A method for stimulating facial nerves in a subject includes providing an electrode having a plurality of contacts, stimulating a central part of a facial nerve with the plurality of contacts in order to improve at least some muscle volume and/or strength in a facial region, and stimulating one or more of the plurality of contacts in order to maintain the muscle volume and/or strength in a desired facial muscle. Another method for stimulating facial nerves in a subject includes providing an electrode having a plurality of contacts in an ear of the subject, stimulating one or more of the plurality of contacts separately in order to determine which contacts activate which facial muscles, identifying one or more contacts from the plurality of contacts that cause one or more nerve branches to activate a desired facial muscle, and selecting the identified contacts to stimulate the one or more nerve branches.

17 Claims, 12 Drawing Sheets

(56) References Cited

U.S. PATENT DOCUMENTS

| | | | | |
|---|---|---|---|---|
| 5,350,414 | A | 9/1994 | Kolen | 607/62 |
| 5,772,605 | A | 6/1998 | Weijand | 600/547 |
| 6,233,472 | B1 | 5/2001 | Bennett et al. | 600/383 |
| 6,516,227 | B1 | 2/2003 | Meadows et al. | 607/46 |
| 6,892,098 | B2 | 5/2005 | Ayal et al. | 607/48 |
| 6,937,904 | B2* | 8/2005 | Richmond et al. | 607/46 |
| 7,774,068 | B1 | 8/2010 | Lozano | 607/48 |
| 8,792,989 | B2 | 7/2014 | Guntinas-Lichius et al. | 607/48 |
| 2001/0031916 | A1* | 10/2001 | Bennett et al. | 600/383 |
| 2002/0161416 | A1* | 10/2002 | Huang | 607/48 |
| 2003/0045922 | A1* | 3/2003 | Northrop | 607/139 |
| 2003/0055468 | A1 | 3/2003 | Sachs | 607/48 |
| 2005/0085544 | A1* | 4/2005 | Hoskonen et al. | 600/544 |
| 2005/0222626 | A1 | 10/2005 | DiLorenzo | 607/2 |
| 2006/0293723 | A1* | 12/2006 | Whitehurst et al. | 607/48 |
| 2007/0088335 | A1 | 4/2007 | Jolly | 604/891.1 |
| 2007/0179557 | A1* | 8/2007 | Maschino et al. | 607/45 |
| 2008/0147141 | A1 | 6/2008 | Testerman et al. | 607/48 |
| 2012/0143284 | A1* | 6/2012 | Capcelea et al. | 607/57 |

FOREIGN PATENT DOCUMENTS

| | | | |
|---|---|---|---|
| WO | WO 2005/062829 | 7/2005 | |
| WO | WO 2008/097407 | 8/2008 | A61B 5/06 |

OTHER PUBLICATIONS

Broniatowski et al., "An Experimental Model for Complex Dynamic Control of the Reinnervated Face," Eur. Arch. Otorhinolaryngol. (Supp.), pp. S147-S148, 1994.

Broniatowski et al., "Dynamic rehabilitation of the paralyzed face: I. Electronic control of reinnervated muscles from intact facial musculature in the rabbit," Otolaryngol.—Head Neck Surg., vol. 97, No. 5, pp. 441-445, 1987.

Broniatowski et al., "Dynamic rehabilitation of the paralyzed face: II. Electronic control of the reinnervated facial musculature from the contralateral side in the rabbit," Otolaryngol.—Head Neck Surg., vol. 101, No. 3, pp. 309-313, 1989.

Broniatowski et al., "Dynamic rehabilitation of the paralyzed face: III: Balanced coupling of oral and ocular musculature from the intact side in the canine," Otolaryngol.—Head Neck Surg., vol. 105, No. 5, 727-733, 1991.

Guntinas-Lichius, "The facial nerve in the presence of a head and neck neoplasm: assessment and outcome after surgical management," Curr. Opin. Otolaryngol. Head Neck Surg., vol. 12, pp. 133-141, 2004.

Guntinas-Lichius et al., "Diagnostics of diseases and the function of the facial nerve," HNO, vol. 15, pp. 1115-1131, 2004.

Guntinas-Lichius et al., "Factors limiting motor recovery after facial nerve transection in the rat: combined structural and functional analyses," Eur. J. Neurosci., vol. 21, pp. 391-402, 2005.

Moran et al., "Patterns of Facial Nerve Synkinesis," The Laryngoscope, vol. 106, pp. 1491-1496, 1996.

Nicolaidis et al., "Muscle Preservation Using an Implantable Electrical System After Nerve Injury and Repair," Microsurgery, vol. 21, pp. 241-247, 2001.

Otto, "Restoration of Function in the Paralyzed Rabbit Orbicularis Oculi Muscle by Direct Functional Electrical Stimulation," The Laryngoscope, vol. 107, pp. 101-111, 1997.

Peckham et al., "Functional Electrical Stimulation for Neuromuscular Applications," Annu. Rev. Biomed. Eng., vol. 7, pp. 327-360, 2005.

Rothstein et al., "Electronic reanimation of facial paralysis—A feasibility study," Otolaryngology Head Neck Surg., vol. 94, No. 1, pp. 82-85, 1986.

Scholle et al., "A surface EMG multi-electrode technique for characterizing muscle activation patterns in mice during treadmill locomotion," J. Neurosci. Methods, vol. 146, pp. 174-182, 2005.

Somia et al., "Multi-Channel Orbicularis Oculi Stimulation to Restore Eye-Blink Function in Facial Paralysis," Microsurgery, vol. 21, pp. 264-270, 2001.

Stennert, "The Autoparalytic Syndrome—A Leading Symptom of Postparetic Facial Function", Arch. Otorhinolaryngol., vol. 236, pp. 97-114, 1982.

Zealear et al., "Control of Paralysed Axial Muscles by Electrical Stimulation," Acta Otolaryngol., vol. 83, pp. 514-527, 1977.

Zealear et al., "Electrical Pacing of the Paralyzed Human Larynx," Ann. Otol. Rhino. Laryngol., vol. 105, pp. 689-693, 1996.

Zealear et al., "Determination of the optimal conditions for laryngeal pacing with the Itrel II implantable stimulator," Otolaryngol.—Head Neck Surg., vol. 125, No. 3, pp. 183-192, 2001.

Zealear et al., "Reanimation of the Paralyzed Human Larynx With an Implantable Electrical Stimulation Device," The Laryngoscope, vol. 113, pp. 1149-1156, 2003.

Zeng, "Trends in Cochlear Implants", Trends Amplif., vol. 8, No. 1, pp. 1-34, 2004.

European Patent Office, Supplementary European Search Report for European Patent Application No. 09822609.5 dated Apr. 11, 2012, 5 pages.

International Searching Authority, International Search Report and Written Opinion of International Application No. PCT/US2009/061441, dated Dec. 24, 2009, 10 pages.

* cited by examiner

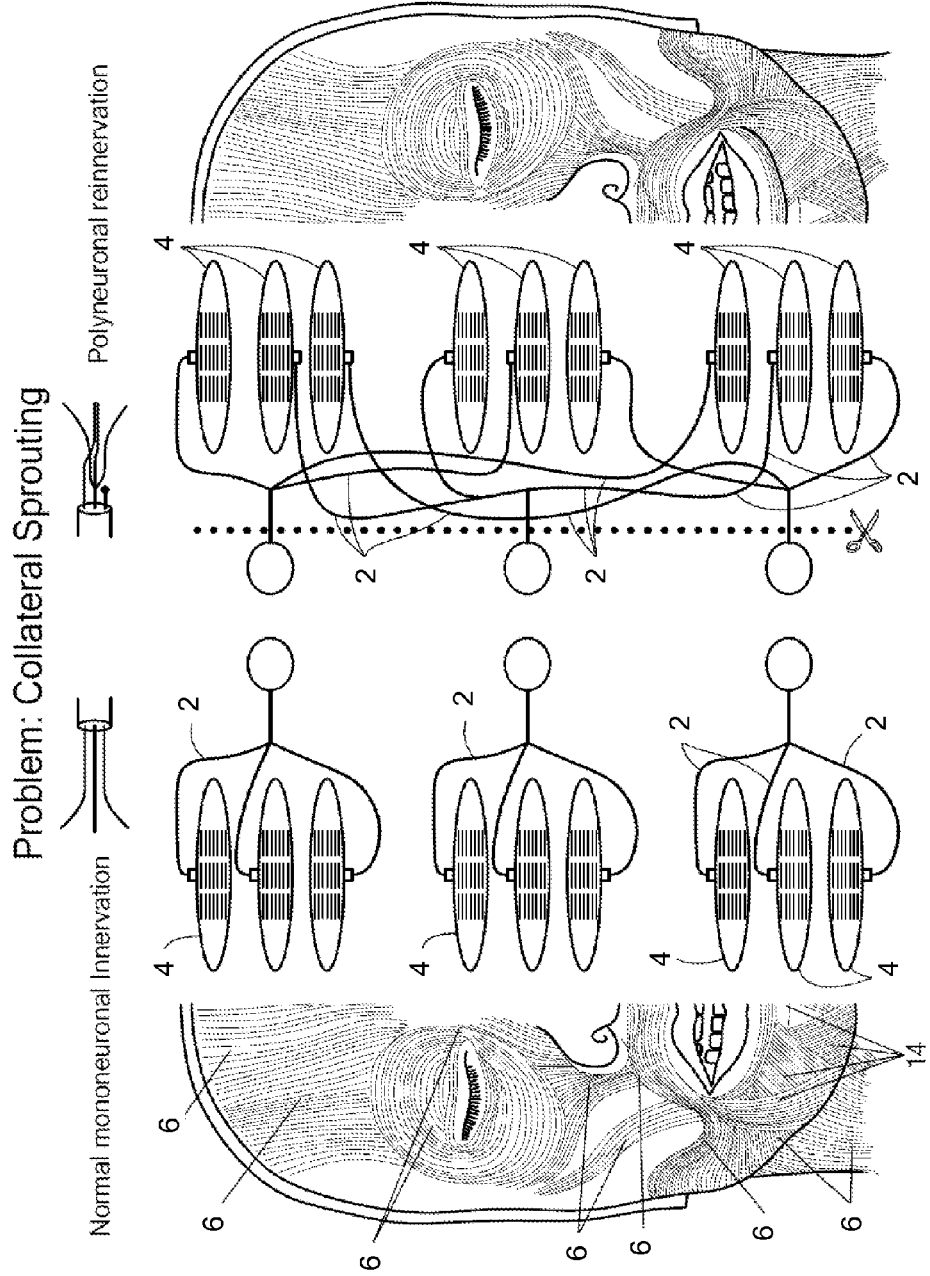

METHOD FOR FACIAL NERVE STIMULATION OF AGING OR DYSFUNCTIONAL MUSCLES

CROSS REFERENCE TO RELATED APPLICATIONS

This patent application is a continuation-in-part of U.S. patent application Ser. No. 12/582,990 filed Oct. 21, 2009, now U.S. Pat. No. 8,792,989, which claims the benefit of U.S. Provisional Patent Application No. 61/107,081 filed Oct. 21, 2008, the disclosures of which are incorporated by reference herein in their entirety.

This patent application also claims the benefit of U.S. Provisional Patent Application No. 61/840,014 filed Jun. 27, 2013, the disclosure of which is incorporated by reference herein in its entirety.

TECHNICAL FIELD

The present invention relates generally to control of muscular activity by electrode stimulation, and in particular, to devices and methods for improving facial muscle volume and/or strength in aging muscles.

BACKGROUND ART

In our society, facial expression is an essential factor of verbal and nonverbal communication. Thus, aging facial muscles can interfere with social and professional success. Aging in the facial region typically means a loss of muscle tone, muscle volume and/or a loss or reduction of connective and fat tissue, e.g., below the eyes and/or at the cheek. As a result of the aging muscles, facial muscles and/or other facial tissues may diminish or atrophy.

There are many problems commonly associated with aging facial muscles. For example, the aging facial muscles can lead people to perceive a person as "old" or "infirm" even though their mental capacity remains intact. In addition, some facial muscle problems that people ascribe to aging, or even to their natural genetic makeup, may be caused or aggravated by other medical problems. It is not surprising that when exercises and medications alone do not provide sufficient improvement, many patients elect more invasive and irreversible surgery, such as face lifts, in an attempt to improve their facial appearance. Even with these consequences, rehabilitation of facial nerves due to aging remains unsatisfactory.

There are also other problems related to dysfunctional facial muscles that can affect a patient's quality of life. Dysfunctional muscles include muscles that do not receive nerve innervation (e.g., due to nerve damage or paralysis), or that do not otherwise fully get stimulated by the nerve for some reason (e.g., synkinetic reinnervated muscles). For example, with facial paresis, patients feel stigmatized and often retreat from the public and develop secondary psychological disorders, e.g., depressions. Thus, the patients' quality of life is significantly curbed. Persistent defects after healing are even observed in cases of spontaneous regeneration or optimal and extensive surgical reconstruction of the nerve in cases of nerve transsection and bridging of the defect with neural transplants. Sprouting of the regenerating axons is observed at the site of the lesion even after reconstruction of nerve continuity. At the same time, Wallerian degeneration of the entire affected section of the nerve as far as the muscles is completed until only the Bungner's bands remain as Schwann cell conducting structures. The regenerating neurons with their sprouting axons grow accidentally into these bands of the individual nerve branches and are directed to the peripheral mimic muscles. Individual axons perish and do not reach the periphery, some accidentally reach their original target muscle, while others reach a completely different target muscle. Due to axonal collateral sprouting, the most frequently observed effect is simultaneous sprouting to several target muscles, such as shown in FIGS. 1A and 1B.

As shown in FIG. 1A, normally exactly one axon 2 projects to one end-plate on the muscle fiber 4. Each of the different muscle groups 6 of the face is activated by the motor neuron pool of a subnucleus of the nucleus. As shown in FIG. 1B, despite transsection and optimal reconstruction of the facial nerve, the regenerating axons 2 may sprout collaterally at the site of the lesion. The axons 2 sprout purely accidentally to any muscle fibers 4. Somatotopic order is lost. This leads clinically to simultaneous movement of several target muscles (a condition called synkinesis). Patients often complain about involuntary lid closure while moving the mouth, e.g., when eating. Simultaneous movement of antagonist muscles leads to the autoparalytic syndrome: muscle forces cancel each other out and no movement is observed clinically despite innervation.

New research shows that not only collateral sprouting but also terminal sprouting of the regenerating axons directly at the neuromuscular end-plates causes uncoordinated muscle function, such as shown in FIGS. 2A and 2B. As shown in FIG. 2A, normally exactly one axon 2 projects to one end-plate on the muscle fiber 4. After transsection and surgical reconstruction, however, terminal sprouting may occur (such as shown in FIG. 2B) in addition to collateral sprouting. In this case, individual end-plates may be activated by several axons 2. Thus, in subjects with these kinds of problems, activating a desired facial muscle may entail considerable challenges since stimulating a nerve branch on the damaged side of the subject's face may not activate the corresponding facial muscle, but an entirely different, unpredictable facial muscle or muscles. This explains why the patients' quality of life is significantly limited even after surgical reconstruction of the nerve. If the lesion is so extensive that the remaining peripheral part of the facial nerve is insufficient, or if Bungner's bands are fibrosed due to failed reinnervation and muscles are atrophied due to long-term denervation of more than 3 to 5 years, the patient can no longer be offered a nerve graft.

Possible therapies include dynamic muscle grafts, free nerve-muscle transplantation, implantation of upper lid weights or static suspensions. Functional results of these secondary procedures are even less satisfactory than the above mentioned nerve grafts. These procedures may, at best, restore muscle tone, but facial expression remains very mask-like and the dynamic muscle suspensions allow reproducing only few and very mechanistic movement vectors.

SUMMARY OF EMBODIMENTS

In accordance with one embodiment of the invention, a method of stimulating facial nerves in a subject with aging muscles includes providing an electrode having a plurality of contacts, stimulating a central part of a facial nerve with the plurality of contacts in order to improve at least some muscle volume and/or strength in a facial region, and stimulating one or more of the plurality of contacts in order to maintain the muscle volume and/or strength in a desired facial muscle.

In accordance with another embodiment, a method of stimulating facial nerves in a subject with dysfunctional facial muscles includes providing an electrode having a plurality of contacts in an ear of the subject, stimulating one or more of the plurality of contacts separately in order to determine which contacts activate which facial muscles, identifying one or more contacts from the plurality of contacts that cause one or more nerve branches to activate a desired facial muscle, and selecting the identified contacts to stimulate the one or more nerve branches.

In accordance with related embodiments, stimulating the central part of the facial nerve may include stimulating a parotid gland region, and/or a region of the facial nerve before it enters a parotid gland region. Stimulating the central part of the facial nerve may be caused by stimulating an outer ear canal region, a middle ear region, and/or a region of the cochlea. The electrode may be a two-dimensional array electrode, a cochlear implant electrode, and/or a rod electrode. The electrode may be provided in an outer ear canal region, a middle ear region, and/or a region of the cochlea. The method may further include selecting one or more contacts to stimulate nerve branches in order to block activation of other facial muscles. The stimulation of the contacts may be triggered based on a sensed signal, e.g., measured using EMG sensors and/or acceleration sensors. The sensed signal may be recorded from sensors placed on or under the subject's skin. The sensed signal may be recorded from a recording electrode having a plurality of contacts placed in the parotid gland region of the subject's face. The facial muscle may be the orbicularis oculi muscle, the orbicularis oris muscle, the occipitofrontalis muscle, the procerus muscle, the nasalis muscle, the depressor septi nasi muscle, the corrugator supercilii muscle, the depressor supercilii muscle, the auricular muscles (anterior, superior, posterior), the depressor anguli oris muscle, the risorius muscle, the zygomaticus major muscle, the zygomaticus minor muscle, the levator labii superioris muscle, the levator labii superioris alaeque nasi muscle, the depressor labii inferioris muscle, the levator anguli oris muscle, the buccinator muscle, and/or the mentalis muscle.

BRIEF DESCRIPTION OF THE DRAWINGS

The foregoing advantages of the invention will be appreciated more fully from the following further description thereof with reference to the accompanying drawings wherein:

FIG. 1A shows a diagram of normal somatotopic organization of facial innervation and FIG. 1B shows the condition after lesion of the facial nerve;

DESCRIPTION OF ILLUSTRATIVE EMBODIMENTS

Figures 2A, 2B:
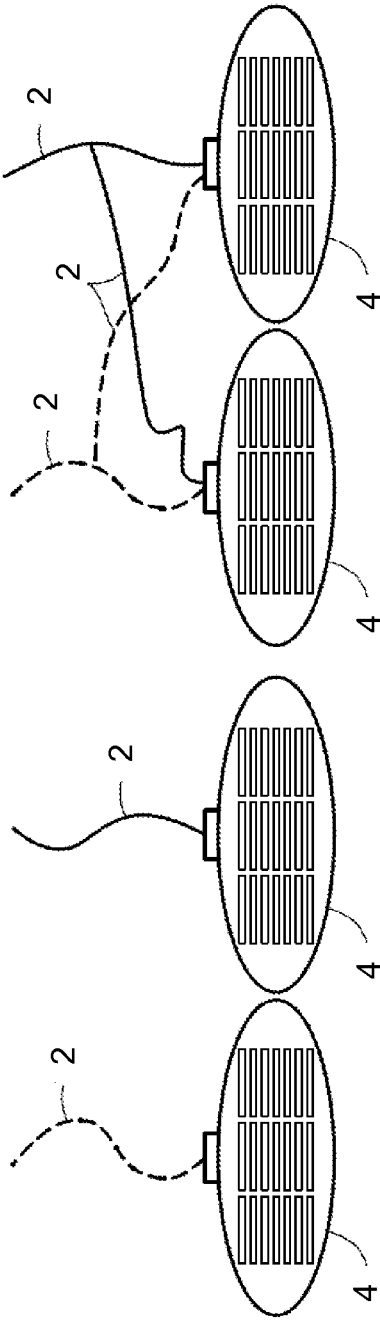
FIG. 2A shows a diagram of a normal end-plate region on a muscle fiber and FIG. 2B shows a diagram of end-plates activated by several axons due to terminal sprouting.

Various embodiments of the present invention address patients suffering from symptoms of aging in regions where the facial nerve controls the muscle tissue. Various embodiments of the present invention also provide a neuroprosthesis placed in an ear region for restoring or partially restoring dysfunctional facial muscles in a subject's face. Accordingly, embodiments provide a method for stimulating a central part of the facial nerve in order to improve, restore, or rehabilitate muscle tone, muscle volume, muscle strength and/or connective and fat tissue due to aging or dysfunctional facial muscles.

In one embodiment, the goal is to bring the muscle tissue back from an atrophied to a nearly non-atrophied condition, and then preserve the non-atrophied condition. In another embodiment, the goal is to restore or partially restore dysfunctional facial muscles in one or both sides of a subject's face. These goal are accomplished by targeting the entire facial region using electrical stimulation of the innervating nerve, i.e., the facial nerve, to excite or activate the muscle tissue in the facial region. This may be accomplished in two different ways. All nerve branches of the parotid gland region may be stimulated at once by an electrode array, e.g., an extended longitudinal or a two-dimensional electrode array. The electrode array may be placed in the parotid gland region where the facial nerve begins to split into a number of individual nerve branches. As known by those skilled in the art, the parotid gland region is a designated part of the face in front of the ear that includes the parotid gland and the structures immediately related to it. In this case, the electrode array may use a fairly unspecific electrical stimulation pattern, e.g., biphasic pulses, in order to activate the facial muscles. Alternatively, the facial nerve may be stimulated before it enters the parotid gland region, and thus before it splits into a number of individual nerve branches, in order to excite/activate the facial muscles. For example, the facial nerve may be stimulated in a region of the facial nerve before it enters a parotid gland region or may be stimulated by stimulating a region of the outer ear canal, a region of the middle ear, and/or a region of the cochlea.

Embodiments may apply electrostimulation in a prescribed manner direct to the desired location in order to stimulate an appropriate or desired region of the facial nerve. Alternatively, activation of the central parts of the facial nerve may be indirectly evoked by reflex activation rather than, or in addition to, direct electrical stimulation. The action potential of the activated muscles may be recorded with a medical device, such as an EMG and/or acceleration sensor. This impulse may then be used to determine when to subsequently stimulate the contacts in order to improve the muscle volume and/or strength of the aging facial muscles. Alternatively, this impulse may then be used to determine which contacts to subsequently select in order to stimulate the appropriate nerves branches to activate the desired facial muscle(s) in a subject with dysfunctional facial muscles. Details of illustrative embodiments are discussed below.

Functional electrostimulation of parts of the body has made considerable progress over the last 40 years. The most extensive experience in the area of ENT medicine is electrostimulation for the cochlear implant. More than 60,000 patients worldwide have received a cochlear implant.

Cochlear implants are the most highly developed electrostimulation implants. They stimulate at 12-24 channels (cardiac pacemakers at 1, pain pacemakers at 4-8) with up to 20,000 pulses per second (cardiac pacemakers with 1, pain pacemakers with up to 190) per channel, up to a maximum of 50,000 Hz. They process incoming signals in various amplitude ranges and frequencies up to 20,000 Hz (at present only cardiac pacemakers with EMG signal recording and foot-drop implants with external heel switches are approved marketed systems with sensors). Cochlear implants are meanwhile also able to measure evoked potentials in the middle ear. The electrodes are thinner and more flexible than cardiac pacemaker electrodes, although they have considerably more recording and stimulation contacts. Developments in cochlear implants led to improved electrodes (reduced risk of breakage, multi-channel systems) and improved stimulation units (miniaturization, implantability).

Figure 3:
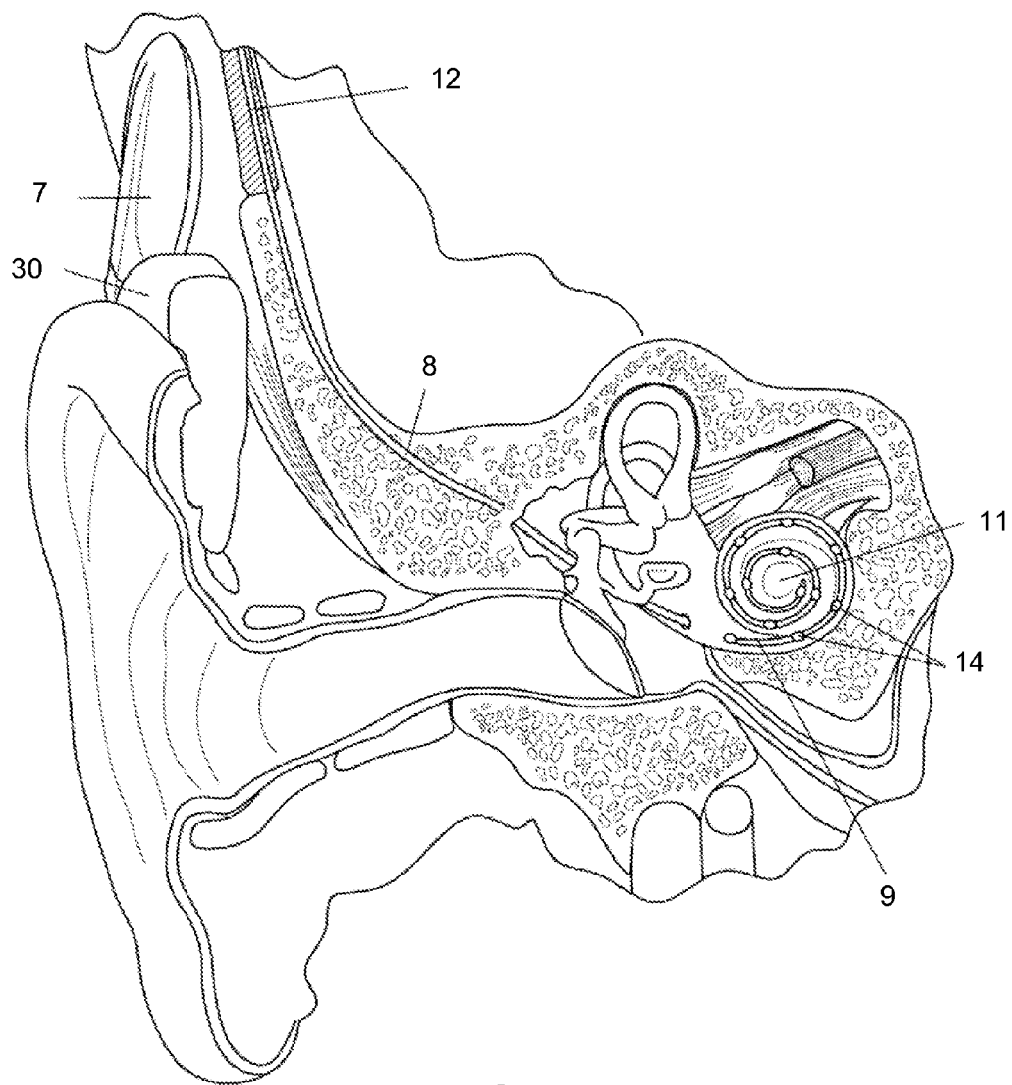
FIG. 3 schematically shows a typical human ear which includes a cochlear implant system.

FIG. 3 schematically shows the anatomy of a normal human ear and some components of a typical cochlear implant system. As shown, the cochlear implant system includes an external microphone (not shown) that provides an audio signal input to an external signal processor 30 where various signal processing schemes may be implemented. The processed signal is then converted into a stimulation pattern by an external transmitter/stimulator 7, and the stimulation pattern/signal is transmitted through connected wires (not shown) to an implanted electrode 12. The electrode 12 has an electrode lead 8 and an electrode array 9. Typically, the electrode array 9 has multiple electrode contacts 14 on its surface that provide selective stimulation to the cochlea 11.

Beside intramuscular electrodes and implantable muscle surface electrodes (epimysial electrodes), extraneural electrodes such as cuff electrodes, epineural and interfascicular electrodes have also been developed. For example, U.S. Pat. No. 7,769,461, incorporated by reference herein, discloses a system and method for applying electrical stimulation to nervous tissue to treat epilepsy, and U.S. Patent App. Publ. No. US2002/0161403, incorporated by reference herein, describes a deep brain stimulation system. These references disclose stimulation systems and some electrical stimulation parameters that may be used with embodiments of the present invention. These electrodes have the advantage of a more selective stimulation of the enclosed nerve at the price of more invasive implantation.

Figure 4:
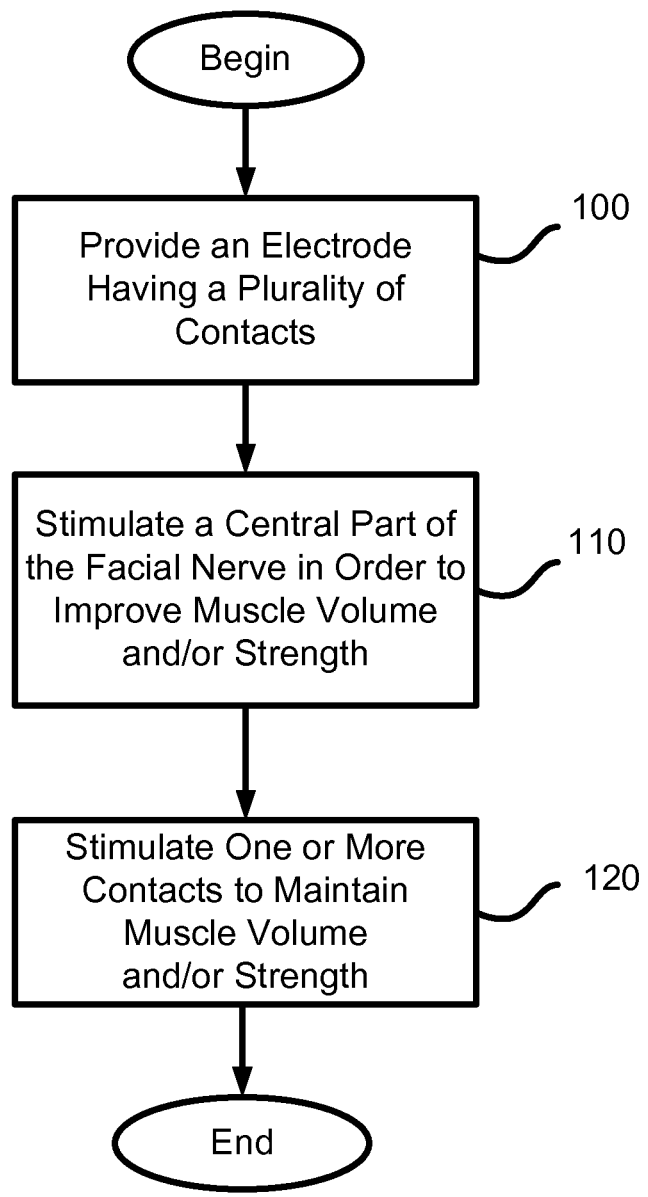
FIG. 4 shows a process of stimulating facial nerves according to embodiments of the present invention.
Figure 5:
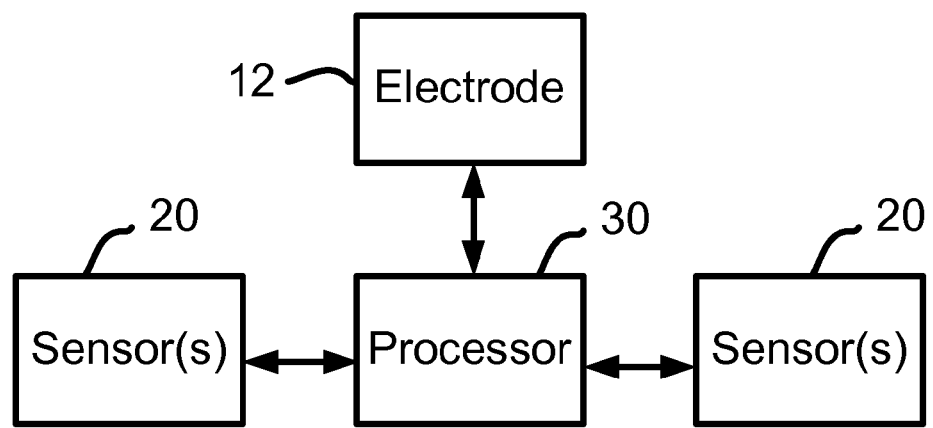
FIG. 5 schematically shows a stimulation system according to embodiments of the present invention.
Figure 6A:
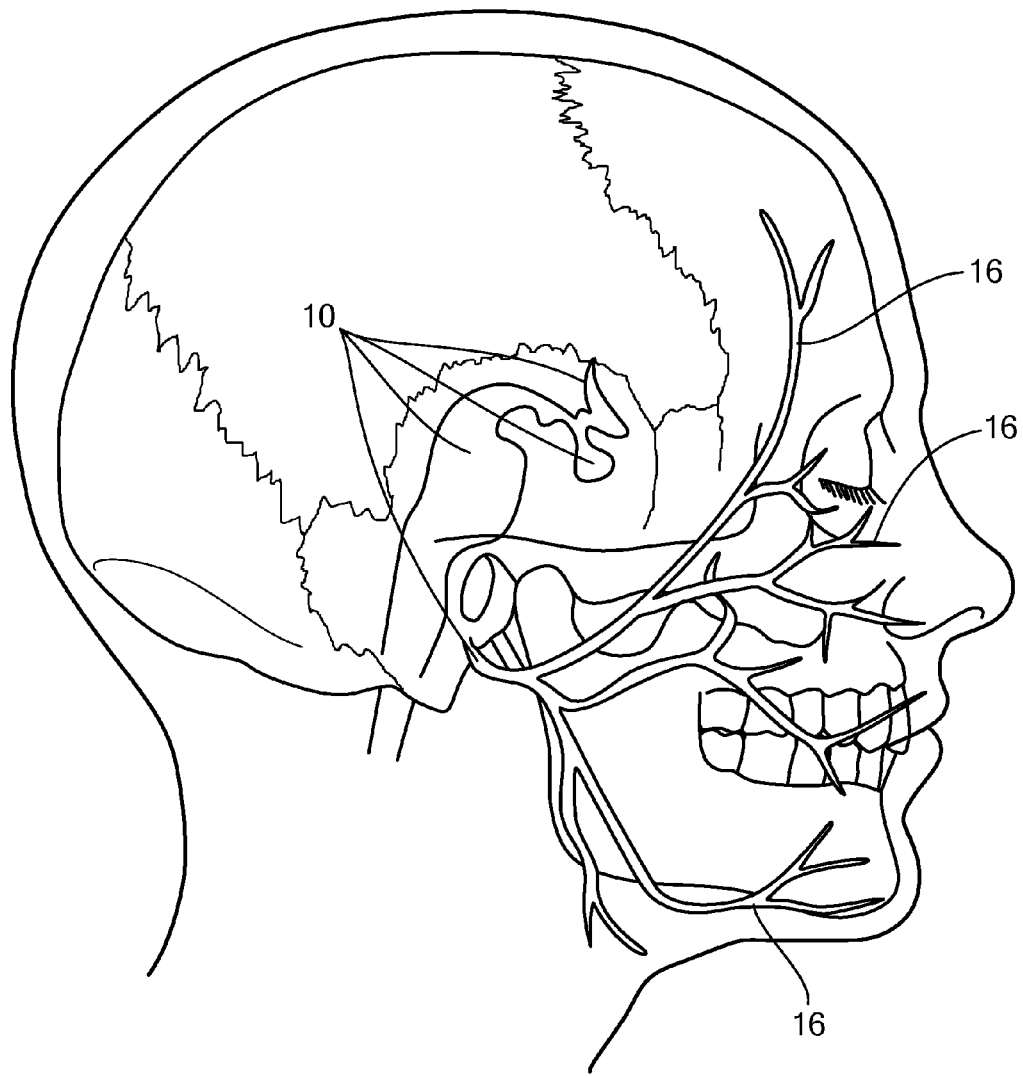
FIGS. 6A through 6D schematically show central parts of the facial nerve according to embodiments of the present invention.
Figure 6B:
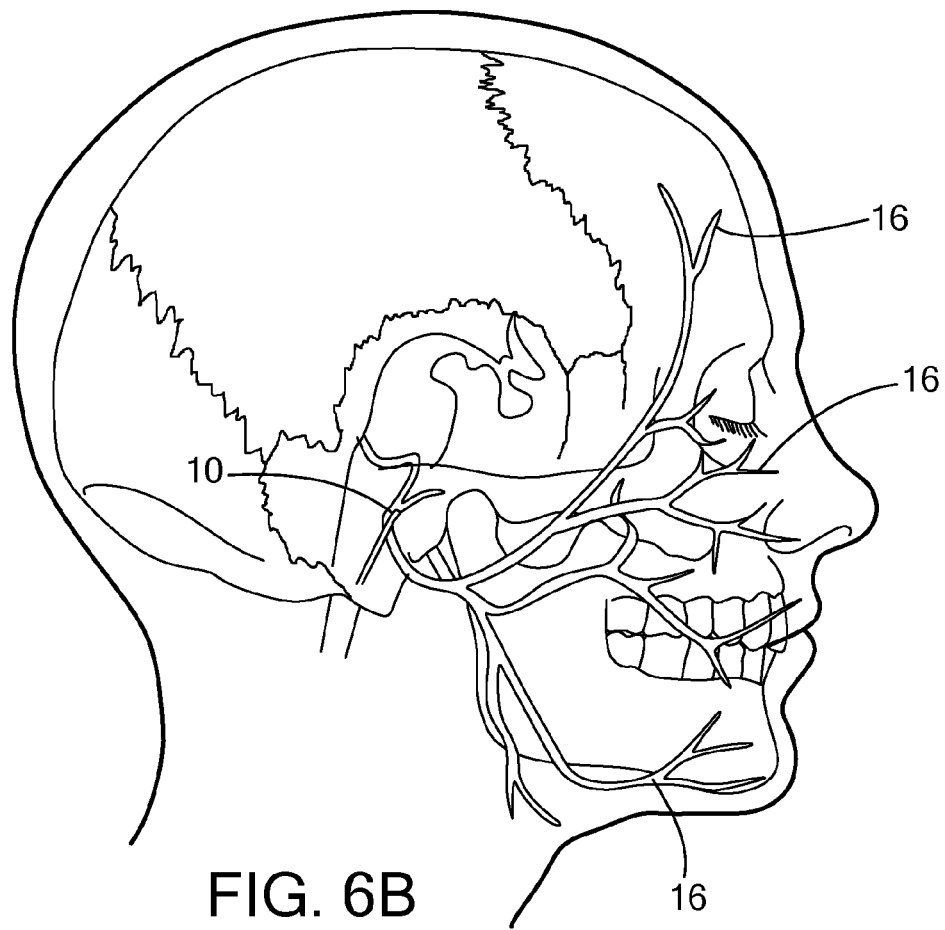
Figure 6C:
Figure 6D:
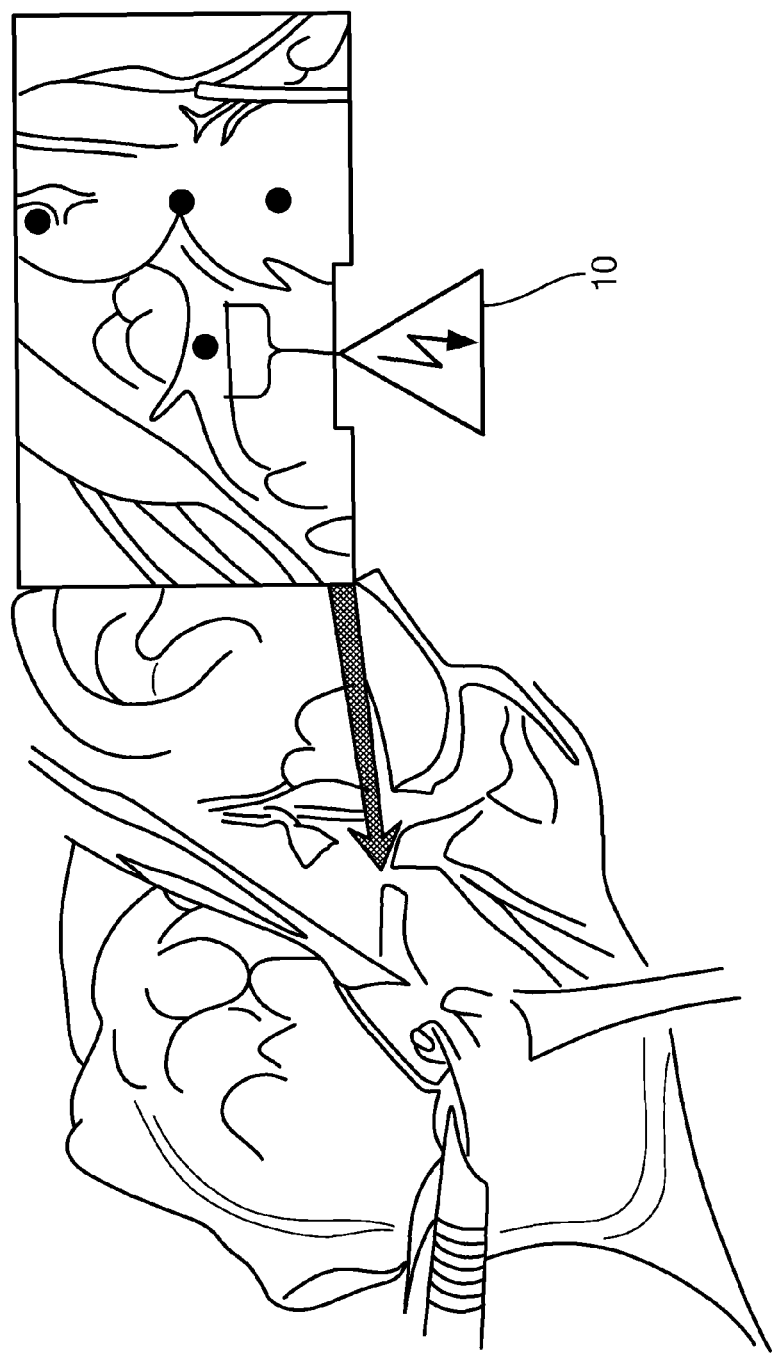
Figure 7:
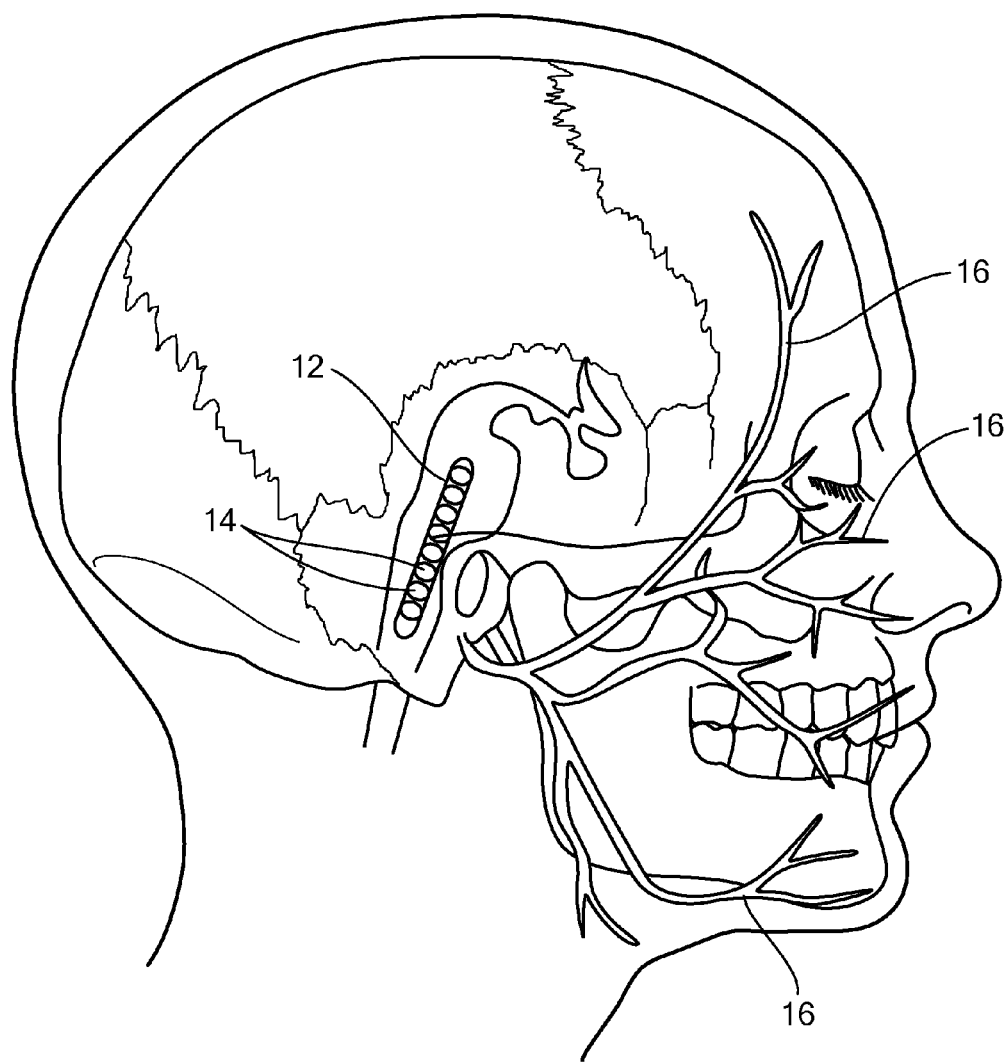
FIG. 7 schematically shows a rod electrode in one central part of the facial nerve according to embodiments of the present invention.
Figure 8:
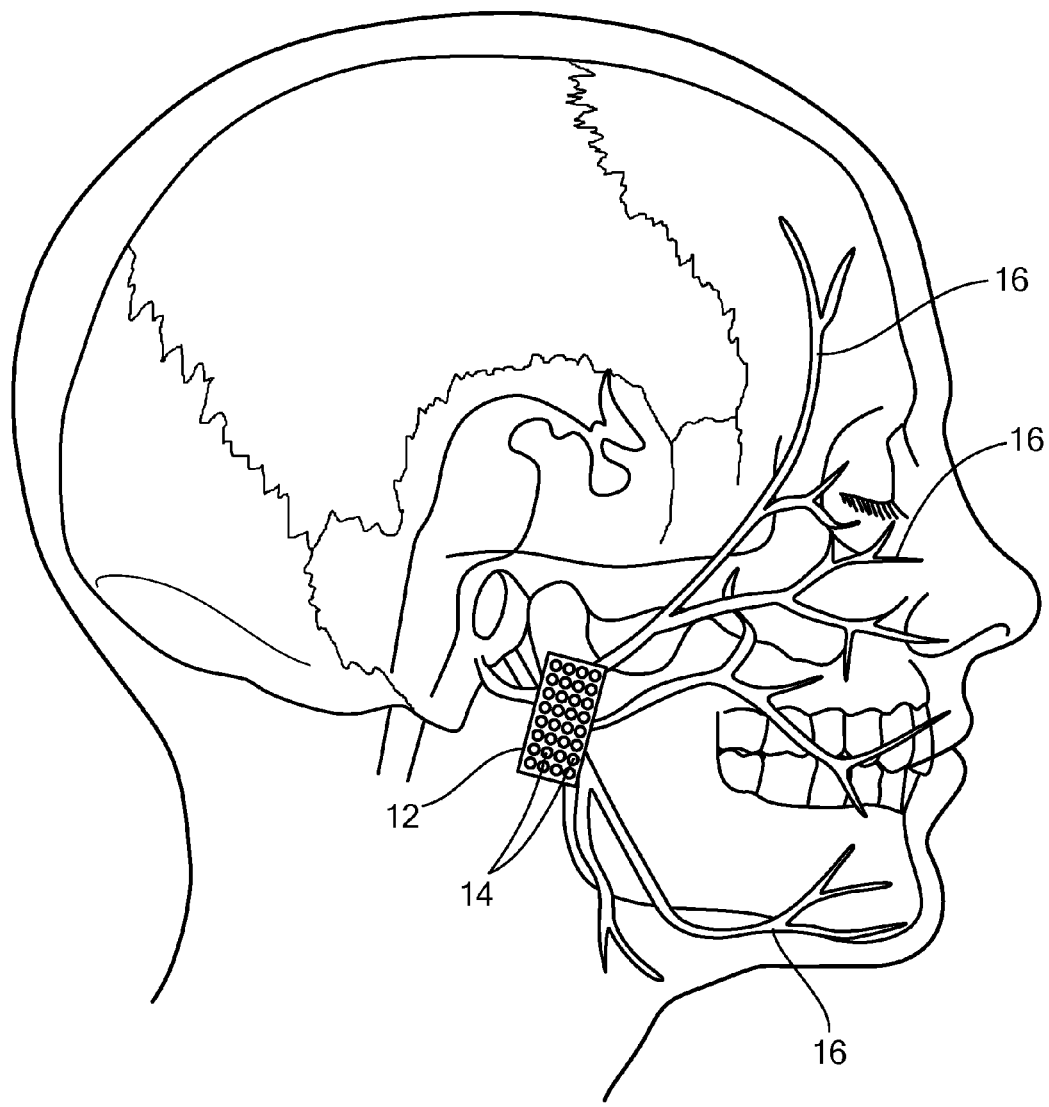
FIG. 8 schematically shows an array electrode in a parotid gland region of the facial nerve according to embodiments of the present invention.

Various embodiments of the present invention provide a system and method of stimulating an appropriate region of the facial nerve in subjects with aging or dysfunctional facial muscles. FIG. 4 shows a process of stimulating facial nerves, and FIG. 5 shows a system for stimulating facial nerves according to embodiments of the present invention. The process begins at step 100, in which an electrode 12 is provided having a plurality of contacts 14, which may be configured in rows and columns (e.g., an array electrode such as shown in FIG. 8), or configured in one or more rows (e.g., one or more rod electrodes such as shown in FIG. 7). The contacts 14 may be used to stimulate a central part of the facial nerve and/or to record nerve impulses or potentials from the nerve branches. For example, FIGS. 6A through 6D show some central parts 10 of the facial nerve that may be stimulated before the facial nerve splits into several nerve branches 16 at the distal part of the facial nerve. As known by those skilled in the art, the electrode 12 may have an insulating electrode pad surrounding the contacts 14 and an electrode lead (not shown) electrically connecting the electrode 12 to a processor 30 for controlling the stimulation and/or recording of the electrode 12.

The processor 30 may also provide signal processing capabilities to the stimulation and/or recording signal information.

In step 110, a central part of the facial nerve is stimulated in order to improve or rehabilitate muscle tone, muscle volume and/or connective and fat tissue that have diminished due to the aging facial muscles. For example, the electrode 12 may be implanted in one of the central parts 10 of the facial nerve before it enters the parotid gland region, such as shown in FIG. 7. A benefit of placing the electrode 12 in this region is that the facial nerve is not yet split into a number of individual nerve branches. Alternatively, the electrode 12 may be implanted in the parotid gland region, such as shown in FIG. 8. A benefit of placing the electrode 12 in this region is that the facial nerve has barely begun to split up into separate nerve branches, allowing the different regions and functions of the face to be innervated with the various contacts 14 in the electrode 12. In general, stimulation in one of the central parts of the facial nerve (e.g., before the parotid gland region or in the parotid gland region) allows the electrode 12 to stimulate the various nerve branches 16 at the same time. The purpose of co-contraction of all muscles of the face substantially simultaneously is to reverse, preserve and counteract ongoing loss of volume and loss of tone of muscles because of age. In addition, the stimulation may reverse or reduce the loss of fat, collagen and/or elasticity in the facial region. The electrode 12 may be implanted above the facial nerve between the nerve and the skin or below the facial nerve. The various contacts 14 may provide the stimulation in a prescribed manner as discussed in more detail below. Alternatively, electrical stimulation of the parotid gland may also provide the benefit of reversing or reducing the loss of fat, collagen and/or elasticity in the facial region.

Once the muscle tone, muscle volume and/or connective and fat tissue has improved or been sufficiently rehabilitated, the electrode 12 stimulates the central parts of the facial nerve, or stimulates various particular branches (or alternatively the parotid gland), in step 120, in order to substantially maintain the improvement from step 110. In steps 110 and/or 120, the movement of the various facial muscles may be measured by optional sensors 20 placed on the skin or implanted under the skin. The sensors 20 may be electromyographic (EMG) sensors, acceleration sensors, or other sensors that may effectively measure muscle movement as is well known to those skilled in the art. The sensors 20 may be in communication with the processor 30 so that the electrode stimulation information is correlated with the measured muscle movement information in order to determine appropriate stimulation parameters. For example, when the electrode array is placed in the parotid gland region, the array may use a fairly unspecific electrical stimulation pattern, e.g., biphasic pulses, in order to activate the facial muscles. The contacts 14 may be stimulated in a sequential manner or in any order or pattern which would provide the desired stimulation parameters.

The processor 30 may determine when or how to stimulate the contacts 14 based on the measured muscle movement information. The processor 30 may then select the appropriate stimulation parameter and stimulate the contacts 14. As shown in FIG. 8, one or more contacts 14 in the electrode array 12 may be stimulated simultaneously in order to activate or excite the facial muscles.

In some situations, the processor 30 may stimulate the contacts 14, either continuously or non-continuously, with a fixed stimulation protocol without further sensor input. When using sensor input, the facial movement information may, optionally, undergo amplification and/or modulation of the signal in a stimulation unit (not shown), which may be in communication with the processor 30. The processor 30 may record or determine which muscles moved and determine a stimulation protocol based on the muscle movement in order to improve the muscle volume and/or strength or maintain the muscle volume and/or strength.

Figure 9:
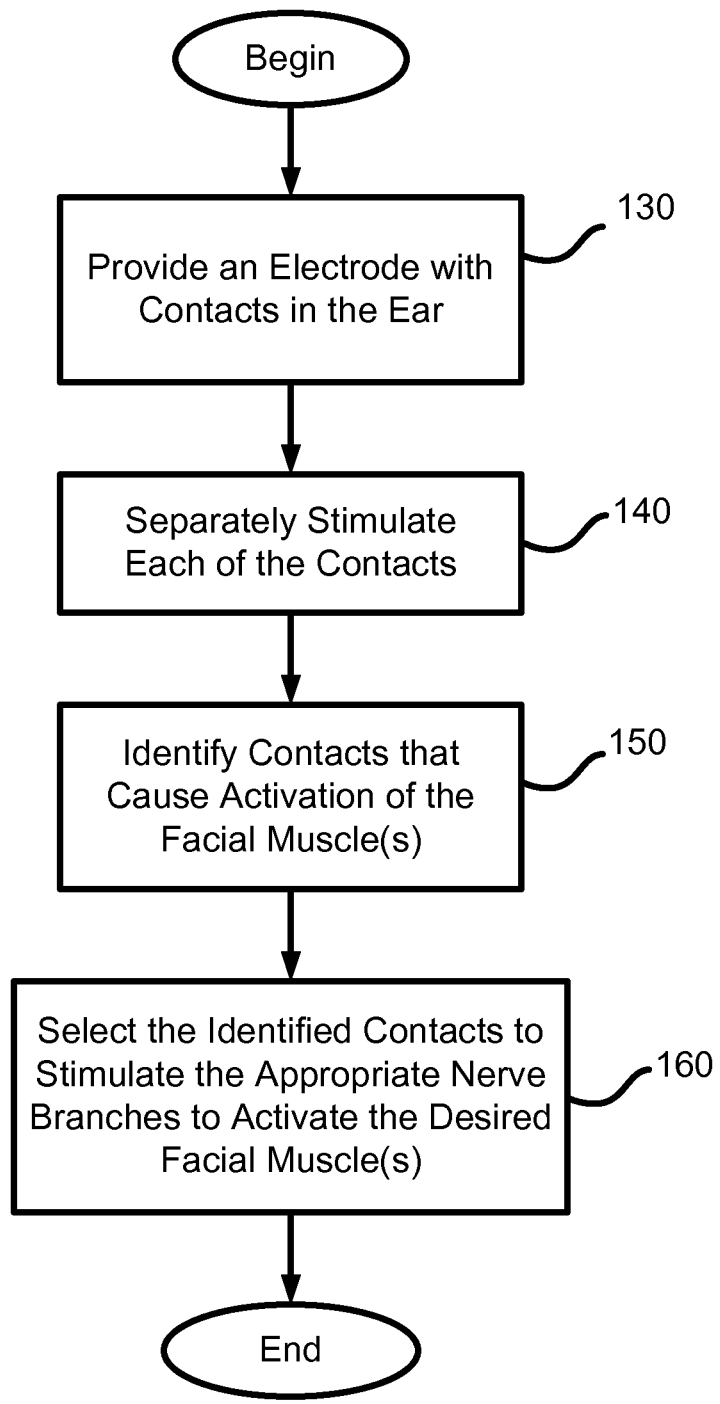
FIG. 9 shows a process of activating facial muscles according to embodiments of the present invention.
Figure 10:
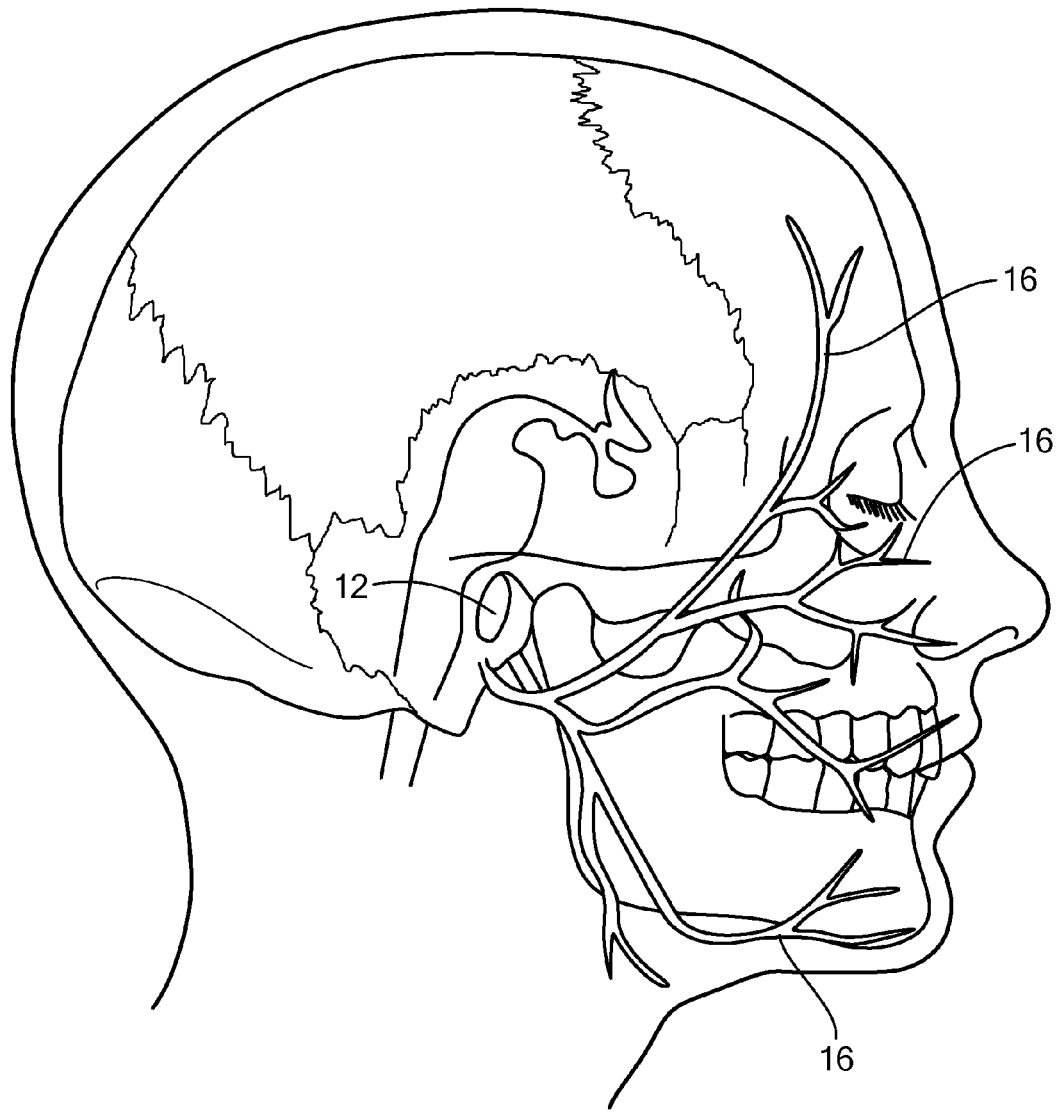
FIG. 10 schematically shows an electrode in regions of the outer ear canal, the middle ear, and/or the cochlea according to embodiments of the present invention.

FIG. 9 shows a process of activating facial muscles in a subject with dysfunctional facial muscles, and FIG. 5 shows a system for activating the facial muscles according to embodiments of the present invention. The process begins at step 130, in which an electrode 12 is provided, having a plurality of contacts 14, in a region of the outer ear canal, a region of the middle ear, and/or a region of the cochlea, such as shown in FIG. 10. For example, the electrode 12 may be a cochlear implant electrode, such as shown in FIG. 3. The contacts 14 may be used to stimulate regions of the ear in order to cause stimulation of a central part of the facial nerve and/or to record nerve impulses or potentials from the nerve branches. As discussed above, the electrode 12 may have an insulating electrode pad surrounding the contacts 14 and an electrode lead 8 electrically connecting the electrode 12 to a processor 30 for controlling the stimulation and/or recording of the electrode 12. The processor 30 may also provide signal processing capabilities. The various contacts 14 may provide the stimulation or recording sequentially or simultaneously, in a prescribed manner as discussed in more detail below.

In step 140, each of the contacts 14 in the electrode 12 is stimulated separately in order to determine which facial muscles are activated. The movement of the various facial muscles may be measured by sensors 20 placed on the skin or implanted under the skin. The sensors 20 may be electromyographic (EMG) sensors, acceleration sensors, or other sensors that may effectively measure muscle movement as is well known to those skilled in the art. The sensors 20 are in communication with the processor 30 so that the contact stimulation information is correlated with the measured muscle movement information in order to determine which contact(s) 14 ultimately activated which facial muscle(s). The contacts 14 may be stimulated in a sequential manner (e.g., the first contact at the proximal end of the electrode, then the next contact along the electrode or the first contact at the distal end of the electrode, then the next contact along the electrode, etc.) or in any order or pattern which would provide the desired information so long as one contact 14 is stimulated at a time. Along with the separate stimulation, a combination of contacts 14 may also be tested to see if two or more contacts simultaneously together activate a particular facial muscle or muscles.

This initial assessment is especially important in subjects with dysfunctional facial muscles, such as synkinetic reinnervated muscles. For example, in a subject with normal somatotopic organization of facial innervation, nerve branch(es) for the eye would activate facial muscle(s) for the eye, and nerve branch(es) for the mouth would activate facial muscle(s) for the mouth, etc. However, in subject's with synkinetic reinnervated muscles, nerve branch(es) for the eye might activate other facial muscle(s) (e.g., facial muscles for the mouth or facial muscles for the mouth and the eye). Thus, by testing via stimulating each contact 14 of the electrode 12 separately, one or more contacts 14 are identified (in step 150) which activate a particular facial muscle, e.g., muscle fibers responsible for closing the eye. If co-activation of other nerve branches happens at an unacceptable level, then one or more contacts 14 may even be used to block the other nerve branches. For example, if one contact stimulates nerve branch a+b, and another contact stimulates branch b, than a distal blocking stimulation of branch b combined with a proximal stimulation of branch a+b may selectively stimulate just branch a. The nerve blocking may be accomplished in a number of ways, such as nerve collision blocking, anodal blocking, high frequency blocking, etc.

In step 160, the identified contacts 14 are selected to stimulate the appropriate nerve branch(es) in order to activate a desired facial muscle(s). The processor 30 may determine which nerve branch(es) are the appropriate ones based on the measured muscle movement information. The processor 30 may then select and stimulate the identified contacts 14. For example, one or more contacts 14 may be stimulated simultaneously in order to activate one or more desired facial muscles. Two or more sets of contacts 14 may also be stimulated together to activate one or more facial muscles at the same time. For example, if one or more contacts are identified to activate a first facial muscle and one or more contacts are identified to activate a second facial muscle, then the first and second set of contacts may be selected at the same time to activate both facial muscles. The two sets of contacts may have some contacts in common, may be completely different contacts, or be the same contacts, depending on the subject's initial assessment.

In certain situations, such as in subjects with facial palsy, the processor 30 may continuously stimulate the identified contacts 14 with a fixed stimulation protocol without further sensor input, e.g., trigger signals from a healthy side of the face. This continuous stimulation may allow the nerve function to maintain or recover the resting tone of a hemiparalyzed face, since the asymmetry of the face at rest is typically the most striking stigma attracting the interest of other people.

The initial assessment from the subject's face may include information from a dysfunctional side and/or a health side of the subject's face. For example, an initial assessment from the dysfunctional side of the subject's face may be used in conjunction with facial movement information from the healthy side of the face. The initial assessment may ensure that the movement sensed on the healthy side triggers the appropriate muscle movement on the dysfunctional side. The facial movement information may, optionally, undergo amplification and/or modulation of the signal in a stimulation unit (not shown), which may be in communication with the processor 30. For example, the processor 30 may record or determine which muscles were moved on the healthy side of the face, determine which contact(s) 14 to select to cause movement of the desired facial muscles on the dysfunctional side of the face, and then select those contact(s) 14 to stimulate the appropriate nerve branches to activate the desired facial muscles.

For example, the initial assessment may determine that the first and third contacts 14 in the electrode 12 placed in the ear cause activation of the facial muscle(s) for the mouth and that the second contact 14 causes activation of the facial muscle(s) for the eye. When the sensors 20 measure that the facial muscle(s) for the eye have moved on the healthy side of the face, the processor 30 selects the second contact 14 in the electrode 12 in order to stimulate the appropriate nerve branch(es) that activate the facial muscle(s) for the eye on a dysfunctional side of the face. Similarly, when the sensors 20 measure that the facial muscle(s) for the mouth have moved on the healthy side of the face, the processor 30 selects the first and third contacts 14 in the electrode 12 in order to stimulate the appropriate nerve branch(es) that activate the facial muscle(s) for the mouth on a dysfunctional side of the face. Electrodes 12 may be placed in one or both of the subject's ears.

A cochlear implant electrode is shown in FIG. 3, and an array electrode and a rod electrode are shown in FIGS. 7 and 8, but other various shapes, like cuff electrodes, and numbers of the electrodes 12 may also be used. For example, two or more rod electrodes 12, each with contacts 14 in a row, may be used to stimulate the central part of the facial nerve in the subject.

Some embodiments of the processor 30 may be implemented as hardware, software (e.g., a computer program product), firmware, or a combination of software, hardware and/or firmware. For example, embodiments may be implemented as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions may embody all or part of the functionality previously described herein with respect to the processor. Those skilled in the art should appreciate that such computer instructions may be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web).

Although the above discussion discloses various exemplary embodiments of the invention, it should be apparent that those skilled in the art can make various modifications that will achieve some of the advantages of the invention without departing from the true scope of the invention.

What is claimed is:

1. A method of stimulating facial nerves in a subject with aging muscles, the method comprising:
    providing an electrode having a plurality of contacts;
    stimulating a central part of a facial nerve, including the parotid gland region, with the plurality of contacts in order to improve at least some muscle volume and/or strength in a facial region; and
    stimulating one or more of the plurality of contacts in order to maintain the muscle volume and/or strength in a desired facial muscle.

2. The method of claim 1, wherein stimulating the central part of the facial nerve is further caused by stimulating a region of outer ear canal.

3. The method of claim 1, wherein stimulating the central part of the facial nerve is further caused by stimulating a region of middle ear.

4. The method of claim 1, wherein stimulating the central part of the facial nerve is further caused by stimulating a region of cochlea.

5. The method of claim 1, wherein the electrode is a two-dimensional array electrode.

6. The method of claim 1, wherein the electrode is a rod electrode.

7. The method of claim 1, wherein the electrode is a cochlear implant electrode.

8. The method of claim 1, wherein stimulation of the plurality of contacts is triggered based on a sensed signal.

9. The method of claim 8, wherein the sensed signal is recorded from sensors placed on or under the subject's skin.

10. A method of stimulating facial nerves in a subject with aging muscles, the method comprising:
    providing an electrode having a plurality of contacts;
    stimulating a central part of a facial nerve before it enters a parotid gland region with the plurality of contacts in order to improve at least some muscle volume and/or strength in a facial region; and
    stimulating one or more of the plurality of contacts in order to maintain the muscle volume and/or strength in a desired facial muscle.

11. A method of stimulating facial nerves in a subject with dysfunctional facial muscles, the method comprising:
    providing an electrode in an ear of the subject, the electrode having a plurality of contacts;
    providing a recording electrode in a parotid gland region of the subject's face;
    stimulating one or more of the plurality of contacts separately in order to determine which contacts activate which facial muscles in the subject;
    identifying one or more contacts from the plurality of contacts that cause one or more nerve branches to activate a desired facial muscle; and
    selecting the identified contacts to stimulate the one or more nerve branches, wherein the stimulation of the one or more nerve branches is triggered based on a sensed signal recorded from the recording electrode.

12. The method of claim 11, wherein the electrode is provided in an outer ear region.

13. The method of claim 11, wherein the electrode is provided in a middle ear region.

14. The method of claim 11, wherein the electrode is provided in a cochlea.

15. The method of claim 11, further comprising selecting one or more contacts to stimulate nerve branches in order to block activation of other facial muscles.

16. The method of claim 11, wherein the recording electrode has a plurality of contacts.

17. The method of claim 11, wherein the sensed signal is recorded from sensors placed on or under the subject's skin.

* * * * *